United States Patent
Cai et al.

(10) Patent No.: US 10,304,320 B2
(45) Date of Patent: May 28, 2019

(54) SYSTEMS, METHODS, AND DEVICES FOR CALIBRATING PARTICULATE MATTER SENSORS

(71) Applicants: Honeywell International Inc., Morris Plains, NJ (US); Kevin Cai, Shanghai (CN); Junfeng Wang, Shanghai (CN)

(72) Inventors: Kevin Cai, Shanghai (CN); Junfeng Wang, Shanghai (CN)

(73) Assignee: Honeywell International Inc., Morris Plains, NJ (US)

( * ) Notice: Subject to any disclaimer, the term of this patent is extended or adjusted under 35 U.S.C. 154(b) by 0 days.

(21) Appl. No.: 16/063,106

(22) PCT Filed: Dec. 16, 2015

(86) PCT No.: PCT/CN2015/097550
§ 371 (c)(1),
(2) Date: Jun. 15, 2018

(87) PCT Pub. No.: WO2017/101039
PCT Pub. Date: Jun. 22, 2017

(65) Prior Publication Data
US 2019/0012903 A1      Jan. 10, 2019

(51) Int. Cl.
*G08B 17/00*        (2006.01)
*G08B 29/20*        (2006.01)
(Continued)

(52) U.S. Cl.
CPC ......... *G08B 29/20* (2013.01); *G01N 33/0006* (2013.01); *G08B 17/10* (2013.01)

(58) Field of Classification Search
CPC ........ G08B 29/20; G08B 17/03; G08B 21/00; G01N 1/26
(Continued)

(56) References Cited

U.S. PATENT DOCUMENTS

| 6,407,671 | B1 * | 6/2002 | Mulvihill | G08B 17/10 |
| | | | | 340/628 |
| 2009/0039249 | A1 * | 2/2009 | Wang | G01N 15/0205 |
| | | | | 250/287 |

(Continued)

*Primary Examiner* — Tai T Nguyen
(74) *Attorney, Agent, or Firm* — Brooks, Cameron & Huebsch, PLLC

(57) ABSTRACT

System (100) for calibrating particulate matter sensors includes a chamber (102) including a plurality of particulate matter sensors (104-1,104-2,104-3,104-N), a fan (110), a particulate matter source (108), an air cleaner (112), and a reference particulate matter sensor (106), a computing device (114) having a processor (118) and a memory (116) storing instructions which, when executed by the processor (118), cause the processor (118) to activate the particulate matter source (108) and the fan (110) until the reference concentration reaches a threshold, activate the air cleaner (112) responsive to the threshold being reached until the reference concentration reaches a calibration point, receive a respective determined mass concentration from each of the plurality of particulate matter sensors (104-1,104-2,104-3, 104-N) at the calibration point, and calibrate each of the plurality of particulate matter sensors (104-1,104-2,104-3, 104-N) based, at least in part, on a respective relationship between the reference concentration and each determined mass concentration at the calibration point. Methods and devices for calibrating particulate matter sensors are also described.

10 Claims, 2 Drawing Sheets

(51) Int. Cl.
*G01N 33/00* (2006.01)
*G08B 17/10* (2006.01)

(58) Field of Classification Search
USPC .................. 340/628, 629, 630, 632, 508
See application file for complete search history.

(56) References Cited

U.S. PATENT DOCUMENTS

| | | | | |
|---|---|---|---|---|
| 2016/0063833 A1* | 3/2016 | Schultz | .................. | G08B 19/00 |
| | | | | 340/522 |
| 2016/0116389 A1* | 4/2016 | Cooper | .................. | G08B 17/10 |
| | | | | 356/340 |
| 2016/0223437 A1* | 8/2016 | Ajay | ..................... | G01N 15/06 |

* cited by examiner

SYSTEMS, METHODS, AND DEVICES FOR CALIBRATING PARTICULATE MATTER SENSORS

TECHNICAL FIELD

The present disclosure relates to systems, methods, and devices for calibrating particulate matter sensors.

BACKGROUND

A particulate matter (e.g., dust) sensor can be used in indoor air indicators, air cleaners, and air filters, among other air devices. In order to function properly, dust sensors may be calibrated in a controlled environment.

Because discrepancies in electronics, optics, mechanics, and/or air ventilation may exist between calibrations, dust sensors may be calibrated in an environment with a reference sensor that provides proven results. Calibration in such environments may be expensive and/or time consuming under previous approaches that lack automation.

DETAILED DESCRIPTION

Figure 1:
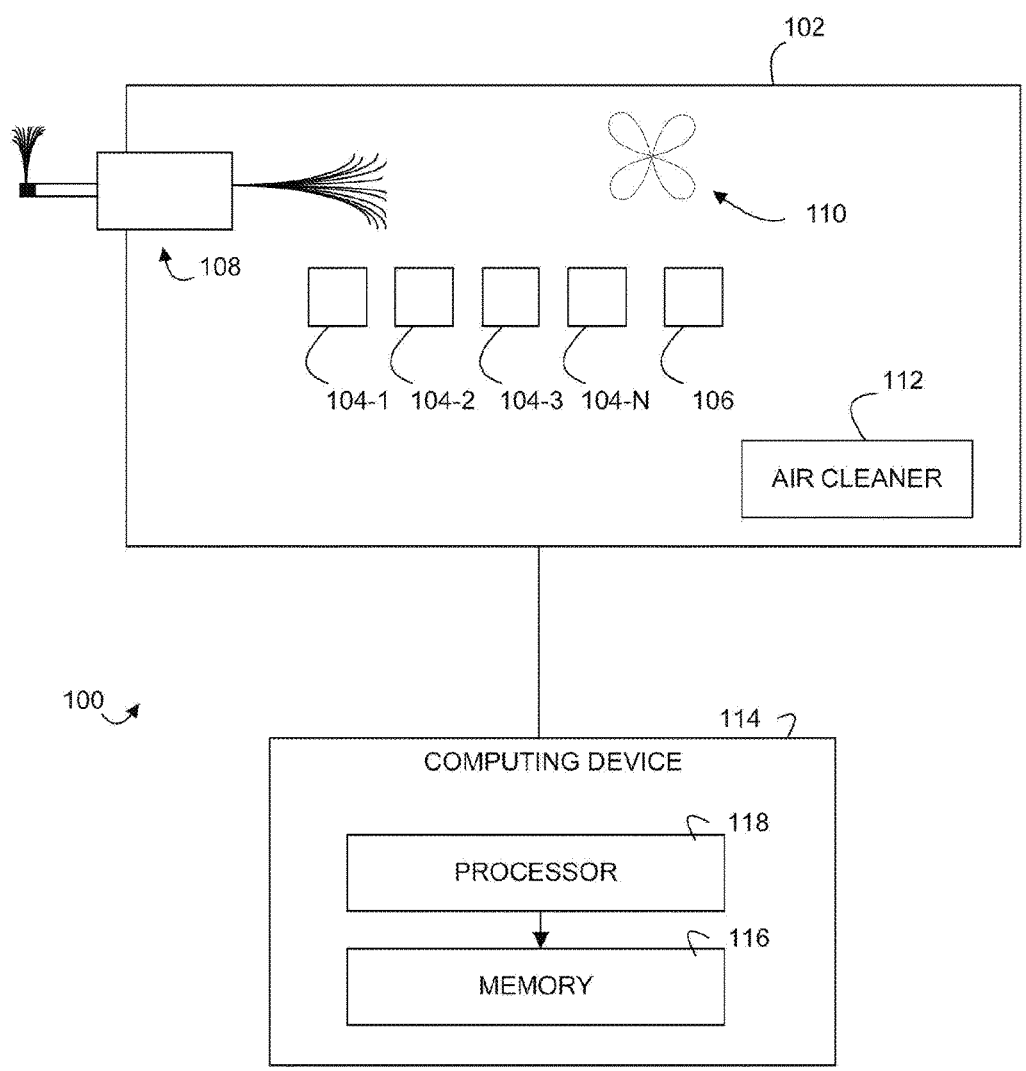
FIG. 1 illustrates a system for calibrating particulate matter sensors in accordance with one or more embodiments of the present disclosure.

Systems, methods, and devices for calibrating particulate matter sensors are described herein. For example, one or more embodiments includes a computing device having a processor and a memory storing instructions which, when executed by the processor, cause the processor to activate the particulate matter source and the fan until the reference concentration reaches a threshold, activate the air cleaner responsive to the threshold being reached until the reference concentration reaches a calibration point, receive a respective determined mass concentration from each of the plurality of particulate matter sensors at the calibration point, and calibrate each of the plurality of particulate matter sensors based, at least in part, on a respective relationship between the reference concentration and each determined mass concentration at the calibration point.

Particulate matter (sometimes referred to herein as "dust") is a particle pollution that can be a mixture of solids and/or liquid droplets in the air. Some particles can be released directly from a specific source, while others form via complex chemical reactions in the atmosphere. The particulate matter can come in a variety of range sizes, including coarse dust particles and/or fine particles. For example, particles less than or equal to 10 micrometers in diameter are small particles which can enter the lungs, potentially causing serious health problems. Particles less than 2.5 micrometers in diameter ($PM_{2.5}$) may be classified as "fine" particles and may pose the greatest health risks.

A dust sensor calibration system can include a chamber (e.g., room), which may be airtight, that accommodates a large number of sensors to be calibrated, a rack to hold the sensors during calibration, a fan to mix dust in the air and maintain a constant dust concentration, an air cleaner to reduce dust concentration, and a reference sensor that can display dust concentration and be used as a "golden reference." In some embodiments, the reference sensor can be a sensor proven to be accurate (or accurate above a particular threshold) under varying dust concentrations.

Embodiments of the present disclosure can increase calibration efficiency, and thus sensor manufacturing efficiency, by automating a number of steps involved in calibration. For instance, according to a number of embodiments, a computing device and/or data acquisition system (DAQ) can control a fan, a reference sensor, an air cleaner, sensors to be calibrated, and a pump that introduces dust to the chamber. In some embodiments, cigarette smoke can be used in calibration.

Embodiments of the present disclosure can automate a number of aspects of sensor calibration. For example, in some embodiments, only lighting a cigarette, attaching the sensors to the rack, and detaching the sensors from the rack involve user interaction.

In some embodiments, once the sensors are installed and the cigarette is lit, the computing device can activate the pump to draw the smoke in the chamber, activate the fan to distribute the smoke throughout the chamber, and monitor the reference sensor to determine when the concentration reaches a first threshold (e.g., high limit). Then, the computing device can activate the air cleaner to reduce the concentration over a period of time.

During that period of time, at pre-defined calibration points, the computing device can deactivate or reduce the operation of the air cleaner and receive determined concentration readings from each sensor being calibrated. When, for instance, the reference concentration reaches a second threshold (e.g., low limit), the computing device can apply one or more curve fitting formulae with respect to the reference sensor to determine coefficients for each sensor being calibrated. Those respective coefficients can be stored in memory (e.g., EEPROM) of each sensor, thus calibrating the sensors. Once calibrated, in some embodiments, the sensors can be tested under similar circumstances and the computing device can determine, for each sensor, whether its accuracy exceeds a threshold and it passes, or its accuracy does not exceed the threshold and it fails.

Such automation can allow embodiments of the present disclosure to calibrate 500 sensors in one half hour, for instance. In some embodiments, 1000-2000 sensors can be calibrated simultaneously during that timeframe.

In the following detailed description, reference is made to the accompanying drawings that form a part hereof. The drawings show by way of illustration how one or more embodiments of the disclosure may be practiced.

These embodiments are described in sufficient detail to enable those of ordinary skill in the art to practice one or more embodiments of this disclosure. It is to be understood that other embodiments may be utilized and that process, electrical, and/or structural changes may be made without departing from the scope of the present disclosure.

As will be appreciated, elements shown in the various embodiments herein can be added, exchanged, combined, and/or eliminated so as to provide a number of additional embodiments of the present disclosure. The proportion and the relative scale of the elements provided in the figures are intended to illustrate the embodiments of the present disclosure, and should not be taken in a limiting sense.

The figures herein follow a numbering convention in which the first digit or digits correspond to the drawing figure number and the remaining digits identify an element or component in the drawing.

As used herein, "a" or "a number of" something can refer to one or more such things. For example, "a number of spikes" can refer to one or more spikes.

FIG. 1 illustrates a system 100 for calibrating particulate matter sensors in accordance with one or more embodiments of the present disclosure. As shown in FIG. 1, system 100 can include a chamber 102 having a plurality of components therein. Those components include a dust sensor 104-1, a dust sensor 104-2, a dust sensor 104-3, and a dust sensor 104-N (cumulatively referred to herein as sensors 104).

Other components in (or partially) in the chamber 102 are a reference sensor 106, a particulate matter source 108 (hereinafter referred to as "pump 108"), a fan 110, and an air cleaner 112. A computing device 114 is shown as being in communication with the chamber 102, though such illustration is made so as not to obscure embodiments of the present disclosure. The computing device 114 can communicate with the components of chamber 102 individually and/or collectively by one or more wired and/or wireless connections. For example, the computing device 114 can receive data from, and/or send data to, the dust sensors 104, the reference sensor 106, the pump 108, the fan 110, and/or the air cleaner 112.

The chamber 102, in some embodiments, can be a room. The chamber 102 can be airtight. For example, the chamber can be a cube-shaped room with sides of 3 meters, though embodiments of the present disclosure are not so limited.

The sensors 104 can be particulate matter (e.g., dust) sensors. The sensors 104 can provide a determination of mass concentration. That is, the air quality and/or air pollution can be calculated as a mass concentration of the fine particles. The mass concentration, air quality, and/or pollution can be provided via a digital display, for instance, which may be implemented on the sensors 104 themselves and/or by the computing device 114.

The sensors 104 can be sensors undergoing calibration, for instance. The sensors 104 can be new (recently manufactured). In some embodiments, the sensors 104 may be undergoing recalibration. Dust sensors undergoing calibration in accordance with embodiments of the present disclosure are not limited to a particular make and/or type of dust sensor. In some embodiments, all of the dust sensors 104 are a same type of sensor. In some embodiments, one or more of the dust sensors 104 is different than another of the dust sensors 104. Embodiments herein are not limited to a particular number of the sensors 104.

Though not shown in FIG. 1, the sensors 104 can be attached to a rack, for instance. In some embodiments, the sensors 104 can be electronically coupled to the rack (e.g., using a micro USB connection) and the rack can be in communication with the computing device 114 via a serial bus (e.g., RS-485). The rack can include a processor (e.g., a microprocessor) and one or more multiplexers.

The reference sensor 106 can be a dust sensor known to provide accuracy, for instance. Accuracy can refer to sensing efficacy exceeding a particular threshold under varying dust concentrations. In some embodiments, the reference sensor 106 is a same type of sensor as one or more of the sensors 104. In some embodiments, the reference sensor 106 is a different type of sensor than one or more of the sensors 104. Though one reference sensor 106 is shown, embodiments of the present disclosure can include more than one reference sensor 106.

The pump 108 can, when activated by the computing device 114, supply particulate matter to the chamber 102. The pump 108 can draw particulate matter into the chamber 102 from outside the chamber 102. In some embodiments, the pump can draw air from (e.g., through) a lit cigarette causing smoke to be drawn from the cigarette into the chamber 102. The cigarette can be a standardized cigarette or brand. In some embodiments, the cigarette can provide a smoke (e.g., particulate) concentration of 300 micrograms per cubic meter into the chamber 102. Though one pump 108 is shown, embodiments of the present disclosure can include more than one pump. For purposes of illustration, embodiments herein are discussed using the example of cigarette smoke as particulate matter in the chamber 102. However, embodiments of the present disclosure are not so limited and such discussion is not to be taken in a limiting sense.

The fan 110 can, when activated by the computing device 114, distribute the smoke throughout the chamber. The fan 110 can enable the uniform distribution of smoke throughout the chamber 102. Though one fan 110 is shown, embodiments of the present disclosure can include more than one fan.

The air cleaner 112 can be a device that, when activated, removes particulate matter from air. In some embodiments, the air cleaner 112 can be an air purifier. Air cleaners in accordance with the disclosed embodiments are not limited to a particular make or type. Though one air cleaner 112 is shown, embodiments can include more than one air cleaner 112.

It is noted that the relative locations of the components shown in the chamber 102 are not to be taken in a limiting sense. For example, though the fan 110 is shown as being proximal to a ceiling of the chamber 102, the fan can be positioned at other locations.

The computing device 114 can include a memory 116. The memory 116 can be any type of storage medium that can be accessed by a processor 118 to perform various examples of the present disclosure. For example, the memory 116 can be a non-transitory computer readable medium having computer readable instructions (e.g., computer program instructions) stored thereon that are executable by the processor 118 to receive a number of electronic signals.

The memory 116 can be volatile or nonvolatile memory. The memory 116 can also be removable (e.g., portable) memory, or non-removable (e.g., internal) memory. For example, the memory 454 can be random access memory (RAM) (e.g., dynamic random access memory (DRAM) and/or phase change random access memory (PCRAM)), read-only memory (ROM) (e.g., electrically erasable programmable read-only memory (EEPROM) and/or compact-disc read-only memory (CD-ROM)), flash memory, a laser disc, a digital versatile disc (DVD) or other optical storage, and/or a magnetic medium such as magnetic cassettes, tapes, or disks, among other types of memory.

Further, although the memory 116 is illustrated as being located within the computing device 114, embodiments of the present disclosure are not so limited. For example, the memory 116 can also be located internal to another computing resource (e.g., enabling computer readable instructions to be downloaded over the Internet or another wired or wireless connection).

In addition, though the computing device 114 is illustrated as being located external to the chamber 102, in some embodiments, the computing device 114 can be located inside (or partially inside) the chamber 102.

As previously discussed, the computing device 114 can communicate with, and/or control, one or more components of the chamber 102. For example, once the the cigarette is lit, the computing device 114 can activate the pump 108 to draw the smoke in the chamber 102 and activate the fan to distribute the smoke throughout the chamber 102. While the smoke is filling the chamber 102, the computing device 114 can monitor the reference sensor 106 to determine when the reference concentration reaches a first threshold (e.g., numerical value, high limit, etc.). In some embodiments, the computing device can receive reference concentration measurements at a particular interval (or constantly) from the reference sensor 106.

In some embodiments, when the reference concentration determined by the reference sensor 106 reaches a particular numerical level, the computing device 114 can activate the air cleaner 112 to reduce the concentration. In some embodiments the particular level can be related to a desired concentration for sensing. For example, if a desired concentration to be sensed by the sensors 104 is 300 micrograms per cubic meter, the concentration causing activation of the air cleaner 112 can be set at 1000 micrograms per cubic meter. In some embodiments, the concentration causing activation of the air cleaner 112 can be a multiple of the desired concentration (e.g., 3× the desired concentration, 5× the desired concentration, etc.). In some embodiments, when the concentration reaches a maximum level or ceases to increase for a particular period of time, the computing device can activate the air cleaner 112 to reduce the concentration.

The air cleaner 112 reduces the concentration of smoke over a period of time. During that period of time, at or before pre-defined calibration points, the computing device 114 can deactivate or reduce the operation of the air cleaner 112 and receive determined concentration readings from each of the sensors 104. A calibration point refers to a particular value of the reference concentration determined by the reference sensor 106. For example, a set of calibration points can include (in mg/m$^3$): 1000, 895, 800, 700, 600, 500, 450, 400, 350, 300, 250, 200, 150, 100, and 50).

The computing device 114 can deactivate the air cleaner 112 at a particular point (e.g., concentration) before a calibration point is reached to allow the smoke concentration in the chamber 102 to stabilize. For example, if a calibration point is 300 micrograms per cubic meter, the computing device 114 can deactivate the air cleaner at a determined concentration exceeding 300 (e.g., 350). Because the reference concentration may continue to slowly decrease after the air cleaner 112 is deactivated, the calibration point of 300 may be approached slowly and with more control than if the air cleaner 112 were left active. Once the calibration point (e.g., 300) is reached and remains stable for a desired period of time, the computing device 114 can receive respective determined concentrations from each of the sensors 104. Once the concentrations are received, the air cleaner 112 can be re-activated until shortly before the next calibration point is reached. This process can be repeated for each of a plurality of calibration points.

When, for instance, the reference concentration determined by the reference sensor 104 reaches a second threshold (e.g., low limit), each of the sensors 104 can be calibrated. In some embodiments, the second threshold is a particular reference concentration, such as 50 mg/m$^3$. In some embodiments, the reference concentration is zero. In some embodiments, the second threshold is a reference concentration below a particular level (e.g., below a level that sensors 104 and/or reference sensor 106 can determine).

Using the respective determined concentrations for each of the sensors 104 for each of the calibration points, the computing device 114 can apply one or more curve fitting formulae to determine coefficients for each of the sensors 104. Each of the sensors 104 and the reference sensor 106 can have a respective curve associated with a determined concentration at each calibration point. In order for a particular sensor 104 to be calibrated, its curve can be fitted to a curve associated with the reference sensor 106 (e.g., a "reference curve"). In some embodiments, segmented linear curve fitting to the reference curve is performed. In some embodiments, polynomial curve fitting to the reference curve is performed.

The curve fitting results in the determination by the computing device 114 of respective coefficients associated with each of the sensors 104. Coefficients determined for a particular sensor can be communicated back to that sensor and stored in memory (e.g., EEPROM) of the sensor.

Once calibrated, in some embodiments, the sensors 104 can be tested under similar circumstances. For example, the chamber 102 can be re-filled with smoke and the process of sequentially moving through the calibration points can be repeated. Along the way, the computing device 114 can determine, for each of the sensors 104, whether its accuracy exceeds a threshold and it passes, or its accuracy does not exceed the threshold and it fails. In some embodiments, if one or more of a sensor's concentration measurements are not sufficiently close to (e.g., within a particular threshold amount of) those of the reference sensor 106, that sensor can be re-calibrated in some instances, or discarded in others.

Figure 2:
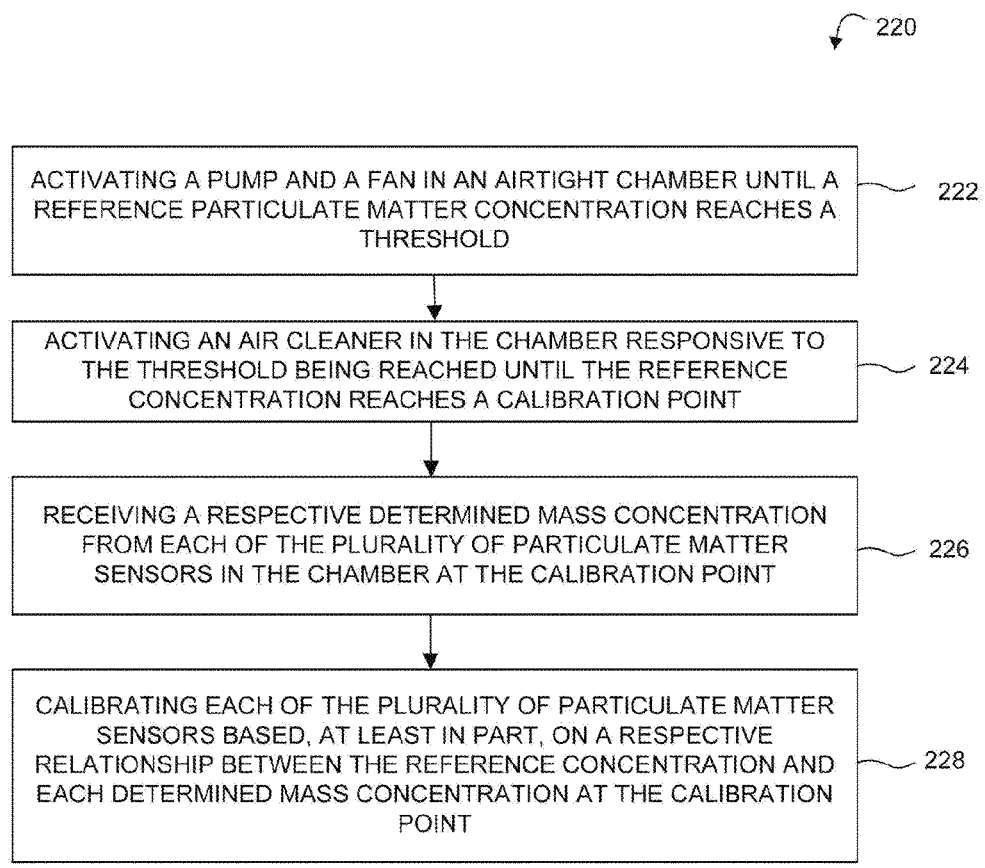
FIG. 2 illustrates a method for calibrating particulate matter sensors in accordance with one or more embodiments of the present disclosure.

FIG. 2 illustrates a method 220 for calibrating particulate matter sensors in accordance with one or more embodiments of the present disclosure. The method 220 can be performed by a computing device (e.g., the computing device 114, previously described in connection with FIG. 1).

At block 222, method 220 includes activating a pump and a fan in an airtight chamber until a reference particulate matter concentration reaches a threshold. The pump can draw cigarette smoke into the chamber, for instance. While the smoke is filling the chamber the reference concentration can be monitored to determine when the reference concentration reaches the threshold, for instance.

At block 224, method 220 includes activating an air cleaner in the chamber responsive to the threshold being reached until the reference concentration reaches a calibration point. The air cleaner can be operated until the calibration point is reached in a manner analogous to that previously discussed in connection with FIG. 1.

At block 226, method 220 includes receiving a respective determined mass concentration from each of the plurality of particulate matter sensors in the chamber at the calibration point. The air cleaner can reduce the concentration of smoke over a period of time. During that period of time, at or before pre-defined calibration points, the air cleaner can be deactivated and determined concentration readings can be received from each of the sensors.

At block 228, method 220 includes calibrating each of the plurality of particulate matter sensors based, at least in part, on a respective relationship between the reference concentration and each determined mass concentration at the calibration point. When, for instance, the reference concentration reaches a second threshold (e.g., low limit), each of the sensors can be calibrated. In some embodiments, the second threshold is a particular reference concentration. One or more curve fitting formulae can be applied to determine coefficients for each of the sensors. Each of the sensors can have a respective curve associated with a determined concentration at each calibration point. In order for a particular sensor to be calibrated, its curve can be fitted to a curve associated with a reference curve. In some embodiments, segmented linear curve fitting to the reference curve is performed. In some embodiments, polynomial curve fitting to the reference curve is performed. The curve fitting results in the determination of respective coefficients associated with each of the sensors. Coefficients determined for a particular sensor can be communicated back to that sensor and stored in memory (e.g., EEPROM) of the sensor.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in example embodiments illustrated in the figures for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed:

1. A system (100) for calibrating particulate matter sensors, comprising:
    a chamber (102) including:
        a plurality of particulate matter sensors (104-1, 104-2, 104-3, 104-N), each configured to determine a mass concentration of a particulate matter in the chamber (102);
        a fan (110) configured to circulate air in the chamber (102);
        a particulate matter source (108);
        an air cleaner (112) configured to remove the particulate matter from the air; and
        a reference particulate matter sensor (106) configured to determine a reference concentration of the particulate matter in the chamber (102); and
    a computing device (114) having a processor (118) and a memory (116) storing instructions which, when executed by the processor (118), cause the processor (118) to:
        activate the particulate matter source (108) and the fan (110) until the reference concentration reaches a threshold;
        activate the air cleaner (112) responsive to the threshold being reached until the reference concentration reaches a calibration point;
        receive a respective determined mass concentration from each of the plurality of particulate matter sensors (104-1, 104-2, 104-3, 104-N) at the calibration point; and
        calibrate each of the plurality of particulate matter sensors (104-1, 104-2, 104-3, 104-N) based, at least in part, on a respective relationship between the reference concentration and each determined mass concentration at the calibration point.

2. The system (100) of claim 1, wherein the particulate matter is cigarette smoke.

3. The system (100) of claim 1, wherein the calibration point is a particular value of the reference concentration determined by the reference sensor (106).

4. The system (100) of claim 1, wherein the respective determined mass concentration is received from each of the plurality of particulate matter sensors (104-1, 104-2, 104-3, 104-N) subsequent to the air cleaner (112) being deactivated for a particular period of time.

5. The system (100) of claim 1, wherein the instructions to calibrate the each of the plurality of particulate matter sensors (104-1, 104-2, 104-3, 104-N) include instructions to fit a concentration curve associated with each of the plurality of particulate matter sensors (104-1, 104-2, 104-3, 104-N) to a reference curve associated with the reference sensor (106).

6. The system (100) of claim 5, wherein the instructions to fit the concentration curve to the reference curve include instructions to perform segmented linear curve fitting.

7. The system (100) of claim 5, wherein the instructions to fit the concentration curve to the reference curve include instructions to perform polynomial curve fitting.

8. The system (100) of claim 5, wherein a plurality of coefficients associated with each fitted concentration curve are stored in a memory of a respective particulate matter sensor (104-1, 104-2, 104-3, 104-N).

9. The system (100) of claim 1, wherein the instructions include instructions to test each of the particulate matter sensors (104-1, 104-2, 104-3, 104-N) subsequent to the calibration of each of the particulate matter sensors (104-1, 104-2, 104-3, 104-N).

10. The system (100) of claim 9, wherein the instructions to test each of the particulate matter sensors (104-1, 104-2, 104-3, 104-N) include instructions to compare a respective determined concentration for each particulate matter sensor (104-1, 104-2, 104-3, 104-N) to a reference concentration at each of a plurality of calibration points.

* * * * *